(12) United States Patent
Mizuno et al.

(10) Patent No.: US 11,761,979 B2
(45) Date of Patent: Sep. 19, 2023

(54) PSYCHOLOGICAL EVALUATION DEVICE, PSYCHOLOGICAL EVALUATION METHOD, PROGRAM, ACCELERATION MEASUREMENT SYSTEM, AND ACCELERATION MEASUREMENT METHOD

(71) Applicants: THE UNIVERSITY OF ELECTRO-COMMUNICATIONS, Chofu (JP); COAMIX INC., Musashino (JP)

(72) Inventors: Tota Mizuno, Chofu (JP); Naoaki Itakura, Chofu (JP); Chisato Amada, Chofu (JP); Nobuhiko Horie, Musashino (JP); Takeshi Hanada, Musashino (JP); Taiyo Nakashima, Musashino (JP)

(73) Assignees: THE UNIVERSITY OF ELECTRO-COMMUNICATIONS, Chofu (JP); COAMIX INC., Musashino (JP)

( * ) Notice: Subject to any disclaimer, the term of this patent is extended or adjusted under 35 U.S.C. 154(b) by 0 days.

(21) Appl. No.: 17/760,912

(22) PCT Filed: Sep. 23, 2020

(86) PCT No.: PCT/JP2020/035701
§ 371 (c)(1),
(2) Date: Mar. 16, 2022

(87) PCT Pub. No.: WO2021/060245
PCT Pub. Date: Apr. 1, 2021

(65) Prior Publication Data
US 2022/0349915 A1    Nov. 3, 2022

(30) Foreign Application Priority Data
Sep. 24, 2019    (JP) .................................. 2019-173151

(51) Int. Cl.
*G01P 15/18*    (2013.01)
(52) U.S. Cl.
CPC .................................. *G01P 15/18* (2013.01)
(58) Field of Classification Search
CPC ....................................................... G01P 15/18
See application file for complete search history.

(56) References Cited

U.S. PATENT DOCUMENTS

| 2009/0312973 A1 | 12/2009 | Hatlestad et al. |
| 2012/0191155 A1 | 7/2012 | Hatlestad et al. |

(Continued)

FOREIGN PATENT DOCUMENTS

| CN | 102792330 A | 11/2012 |
| CN | 105303039 A * | 2/2016 |

(Continued)

OTHER PUBLICATIONS

Kurano et al., "Estimating Video Viewer's Interests by Multi-modal Data Captured by Smartphone", IPSJ SIG Technical Report, 2013.*

(Continued)

*Primary Examiner* — Lina Cordero
(74) *Attorney, Agent, or Firm* — Oliff PLC

(57) ABSTRACT

A psychological evaluation device that estimates interest of a subject in a content used integrally with a terminal held by the subject. Acceleration data obtained by an acceleration sensor built in the terminal is acquired, and a frequency analysis is performed on the acquired acceleration data to obtain acceleration in the gravity direction of the terminal. By obtaining the acceleration in the gravity direction of the terminal, it is possible to, for example, estimate the subject's interest in the content based on the integral value of each frequency component of the acceleration in the gravity direction obtained by performing the frequency analysis.

11 Claims, 14 Drawing Sheets

(56) References Cited

U.S. PATENT DOCUMENTS

| | | | |
|---|---|---|---|
| 2012/0317066 A1 | 12/2012 | Miyazaki | |
| 2013/0252637 A1* | 9/2013 | Cha | H04W 4/021 |
| | | | 455/456.3 |
| 2013/0298636 A1 | 11/2013 | Hatlestad et al. | |
| 2018/0249917 A1* | 9/2018 | Sasahara | A61B 5/7235 |
| 2019/0141492 A1* | 5/2019 | Cha | H04L 67/52 |
| 2019/0265270 A1 | 8/2019 | Yamashita et al. | |

FOREIGN PATENT DOCUMENTS

| | | |
|---|---|---|
| JP | 2016-000153 A | 1/2016 |
| JP | 2018-007265 A | 1/2018 |
| JP | 2019-106033 A | 6/2019 |
| WO | 2011/114620 A1 | 9/2011 |
| WO | 2018/088042 A1 | 5/2018 |

OTHER PUBLICATIONS

Tamura et al., "Recognition experiment of emotional walking motion using accelerometer", J. Japan Society for Intelligent Information, 2010.*

Saito et al., "Proposal of an Algorithm for Video Advertisement Insertion using Smartphone Sensors," Information Processing Society of Japan, 2017.*

Okada et al., "Advertisement Effectiveness Estimation Based on Crowdsourced Multimodal Affective Responses," 2018 IEEE/CVF Conference on Computer Vision and Pattern Recognition Workshops, pp. 1344-1352.*

Gedik et al., "Capturing Interaction Quality in Long Duration (Simulated) Space Missions with Wearables," J. LaTex Class Files, vol. 14, No. 8, Aug. 2015.*

CN105303039A, translation (Year: 2016).*

JP2019106033A, translation (Year: 2019).*

Dec. 21, 2021 International Preliminary Report on Patentability issued in International Application No. PCT/JP2020/035701.

Hong Yan, "Research on a Content Browsing Support Method by Estimating INterest Based on User's Behavior," Kyushu University Institutional Repository, 2015, pp. 1-101.

Daijiro et al., "Estimating Video Viewer's Interests by Multi-modal Data Captured by Smartphone," IPSJ SIG Technical Report, Mar. 7, 2013, vol. 2013-MBL-65, No. 30, pp. 1-8.

Dec. 8, 2020 International Search Report issued in International Patent Application No. PCT/JP2020/035701.

* cited by examiner

FIG. 11

| FREQUENCY BAND (Hz) | SMARTPHONE | | DIFFERENCE | |
|---|---|---|---|---|
| | AVERAGE | VARIANCE | AVERAGE | VARIANCE |
| 1-2 | -0.704 | 0.036 | -0.835 | 0.002 |
| 2-3 | -0.675 | 0.051 | -0.850 | 0.002 |
| 3-4 | -0.812 | 0.027 | -0.795 | 0.003 |
| 4-5 | -0.697 | 0.048 | -0.824 | 0.001 |

|  |  | QUESTIONNAIRE RESULT |
|---|---|---|
| SUBJECT [1] | WORK A | 6 |
|  | WORK B | 5 |
|  | WORK C | 7 |
| SUBJECT [2] | WORK A | 7 |
|  | WORK B | 8 |
|  | WORK C | 7 |
| SUBJECT [3] | WORK A | 4 |
|  | WORK B | 7 |
|  | WORK C | 9 |

PSYCHOLOGICAL EVALUATION DEVICE, PSYCHOLOGICAL EVALUATION METHOD, PROGRAM, ACCELERATION MEASUREMENT SYSTEM, AND ACCELERATION MEASUREMENT METHOD

TECHNICAL FIELD

The present invention relates to a psychological evaluation device, a psychological evaluation method, a program, an acceleration measurement system, and an acceleration measurement method for evaluating preference and the like of a user who is browsing a content.

BACKGROUND ART

Conventionally, with the spread of electronic devices such as smartphones, tablet terminals and the like, digitization of contents has advanced. With the increase of electronic contents, a user has more opportunities to display various contents on the display of an electronic device to browse the displayed contents. The electronic contents include, for example, electronic books, electronic comics, and various kinds of moving images; these electronic contents are displayed on the display of a smartphone or the like so as to be browsed by the user.

When browsing the electronic contents on a smartphone, the user accesses a site that provides (sells) electronic contents, selects a desired electronic content from a list of electronic contents provided by the site, and receives distribution from the site.

Here, the site that provides electronic contents judges the tendency of the contents that the user prefers based on his (or her) past download history and browsing history, and recommends the user the electronic contents considered to match his (or her) preference.

For example, PTL 1 describes a process for determining contents to be recommended to the user based on the number of times the user browses the contents distributed via a network.

Further, NPL 1 describes a method of using a three-dimensional acceleration sensor built in a smartphone to read an acceleration waveform generated when a user browses a content, and evaluating the relationship between the three-dimensional acceleration of the smartphone itself caused by user's behavior when he (or she) browses the content and the user's interest in the content. To be specific, as a concrete example of evaluating the aforesaid relationship, NPL 1 describes that when a content is unlikely to be of interest to the user, distribution of frequency components obtained by performing a Fourier transform on the three-dimensional acceleration is dispersed; whereas when a content is of high interest to the user, distribution of frequency components obtained by performing a Fourier transform on the three-dimensional acceleration is concentrated in the region of low frequency components.

CITATION LIST

Patent Literature

PTL 1: Japanese Unexamined Patent Application Publication No. 2019-106033

Non Patent Literature

NPL 1: Hong Yan, Research on a Content Browsing Support Method by Estimating Interest Based on User's Behavior, Kyushu University Institutional Repository, 2015

SUMMARY OF INVENTION

Technical Problem

As described in NPL 1, it has been conventionally known that, when a user is browsing a content with a smartphone, acceleration data of a three-axis acceleration sensor built in the smartphone can be used to estimate the user's interest in the content being browsed. However, in the conventional method, in order to perform accurate evaluation using the three-axis acceleration sensor built in the smartphone, the user must always maintain a constant posture when holding the smartphone in the hand. To be specific, if the user's posture when holding the smartphone changes, the acceleration waveform acquired by the three-axis acceleration sensor will change just because of the change of the user's posture, and therefore it is impossible to perform accurate evaluation.

Thus, the problem with the conventional method described in NPL 1 is that it requires the user to hold the smartphone in a predetermined posture in order to estimate the user's interests, so that the method is not a highly versatile method for estimating interest. In other words, in the conventional method, since the user is required to hold the smartphone in a manner different from the normal daily life, it is difficult to estimate the user's interest in the content displayed on the smartphone when the smartphone is used in the way of normal daily life.

It is an object of the present invention to provide a psychological evaluation device, a psychological evaluation method, and a program capable of accurately evaluating the interest of a user when the user uses a terminal, such as a smartphone, in the way of normal daily life. Further, it is another object of the present invention to provide an acceleration measurement system and an acceleration measurement method applicable to such psychological evaluation.

Solution to Problem

The psychological evaluation device according to an aspect of the present invention is a psychological evaluation device for estimating interest of a subject in a content used integrally with a terminal held by the subject. The device includes: an acceleration data acquisition unit that acquires acceleration data obtained by an acceleration sensor built in the terminal; a frequency analysis unit that performs a frequency analysis on the acceleration data obtained by the acceleration data acquisition unit; an average calculation unit that calculates an average of each frequency component obtained by performing the frequency analysis by the frequency analysis unit, for a predetermined time; and an evaluation unit that estimates, when the terminal displays a specific content, that the subject's interest in the specific content is high if an integral value of the average of each frequency component calculated by the average calculation unit is smaller than an integral value of the average obtained when the terminal displays a content other than the specific content.

The psychological evaluation method according to another aspect of the present invention is a psychological evaluation method for estimating interest of a subject in a content used integrally with a terminal held by the subject. The method includes: an acceleration data acquisition process for acquiring acceleration data obtained by an acceleration sensor built in the terminal; a frequency analysis process for performing a frequency analysis on the acceleration data obtained in the acceleration data acquisition process; an average calculation process for calculating an average of each frequency component obtained by performing the frequency analysis in the frequency analysis process, for a predetermined time; and an evaluation process for estimating, when the terminal displays a specific content, that the subject's interest in the specific content is high if an integral value of the average of each frequency component calculated in the average calculation process is smaller than an integral value of the average obtained when the terminal displays a content other than the specific content.

The program according to further another aspect of the present invention is a program that implements the procedures for executing each process of the above-mentioned psychological evaluation method in a computer and causes the computer to execute these procedures.

According to the present invention, it is possible to accurately detect vibration caused by physiological tremor of the subject with a simple configuration, and accurately estimate the interest of the subject in the content.

BRIEF DESCRIPTION OF DRAWINGS

FIG. 11 is a table showing an example of the correlation between interestingness of a work and amplitude integral values measured by applying the first and second embodiments of the present invention;

DESCRIPTION OF EMBODIMENTS

1. First Embodiment

A first embodiment will be described below with reference to FIG. 1 to FIG. 6.

[1-1. Application Examples of Psychological Evaluation Device]

Figure 1:
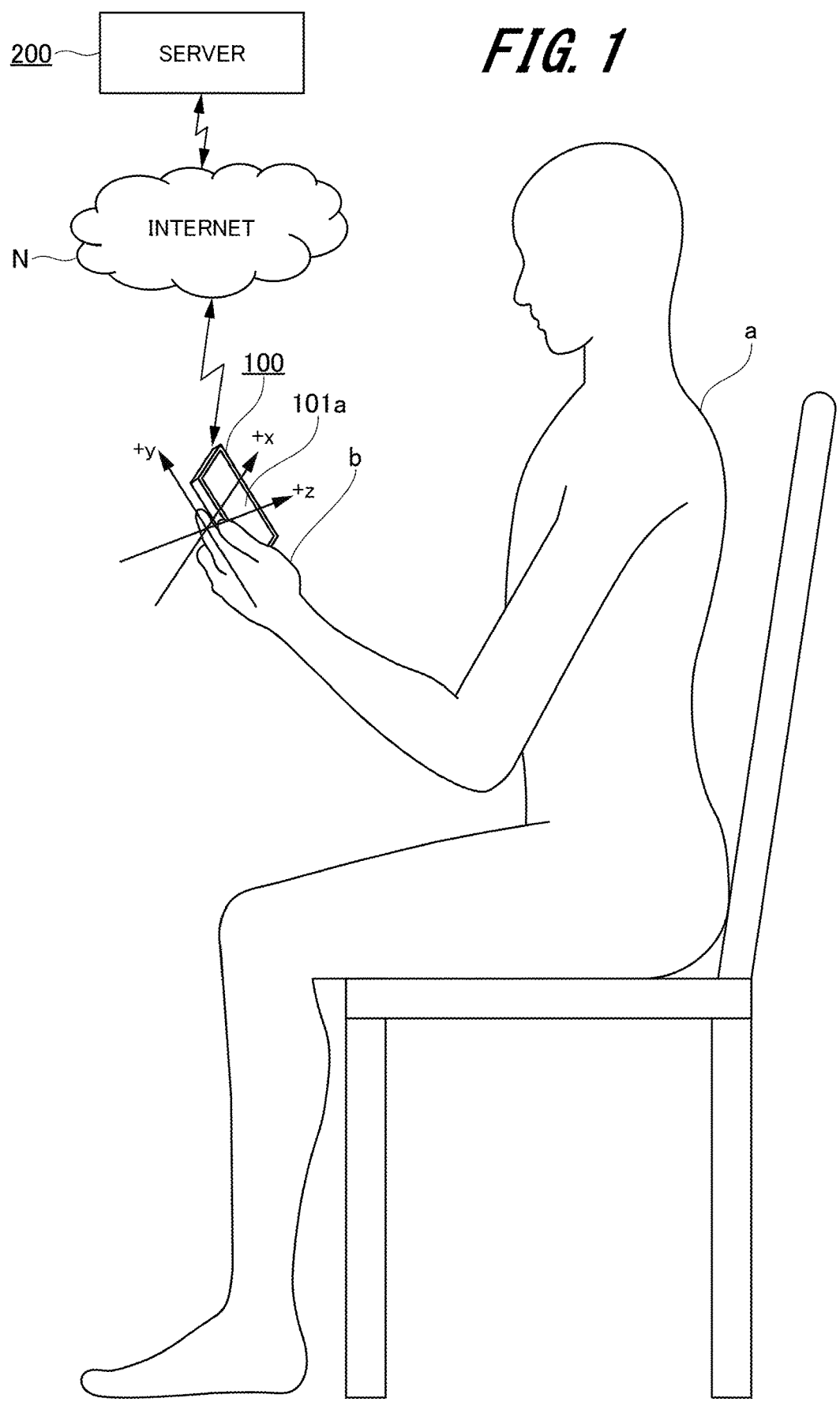
FIG. 1 is a view showing an application example of a psychological evaluation device according to a first embodiment of the present invention.

FIG. 1 is a view showing an application example of a psychological evaluation device according to the present embodiment.

In the present embodiment, a content (an electronic comic or the like) is displayed on a terminal 100 (smartphone) held by a user (i.e., a subject) with one hand, and the terminal 100 (or a server 200) performs psychological evaluation for estimating the interest of the user in the content being browsed.

To be specific, the terminal 100 performs communication, via the Internet N, with the server 200 that distributes the contents, and a screen 101a of a display 101 (see FIG. 2) of the terminal 100 displays the content (an electronic comic, for example) distributed by the server 200. The terminal 100, which is a smartphone, has an application program implemented therein, which causes the terminal 100 to function as a psychological evaluation device.

Here, the terminal 100 is assumed to be held by a hand b of a user a.

The terminal 100 has a three-axis acceleration sensor 105 (see FIG. 2) built therein, and the terminal 100 can detect acceleration of three axes (x-axis, y-axis, and z-axis) when held by the hand b. As shown in FIG. 1, the y-axis of the acceleration (vector) detected by the three-axis acceleration sensor 105 built in the terminal 100 is the longitudinal direction (vertical direction) of the screen 101a, the x-axis is the transverse direction (horizontal direction) of the screen 101a, and the z-axis is a direction perpendicular to the screen 101a.

Note that, in order to simplify the description, the three axes (x-axis, y-axis, and z-axis) are set with respect to the orientation of the screen 101a; however, the three axes of x-axis, y-axis, and z-axis orthogonal to each other may also be set with respect to other orientations such as the gravity direction. For example, the gravity direction (vertical direction) may be set as the y-axis, and two axes orthogonal to the gravity direction may be set as the x-axis and the z-axis. These three axes of x-axis, y-axis, and z-axis orthogonal to each other are set by the three-axis acceleration sensor 105.

In the present embodiment, a vibration, referred to as physiological tremor, of the hand b of the user a is detected by the three-axis acceleration sensor 105 built in the terminal 100.

The physiological tremor is a vibration caused by repeated contraction and relaxation of muscles; it occurs even in healthy people, and is different from tremor caused by some disease or disorder. However, the physiological tremor is a very small vibration, so that healthy people are usually not aware of it.

The frequency of the physiological tremor is known to be as low as 10 Hz, for example, but it varies depending on the part of the body. For example, in the hand beyond the wrist, the primary frequency of the vibration in the gravity direction caused by the physiological tremor is in a range of 2.5 Hz to 3.5 Hz.

[1-2. Examples of Device Configuration]

Figure 2:
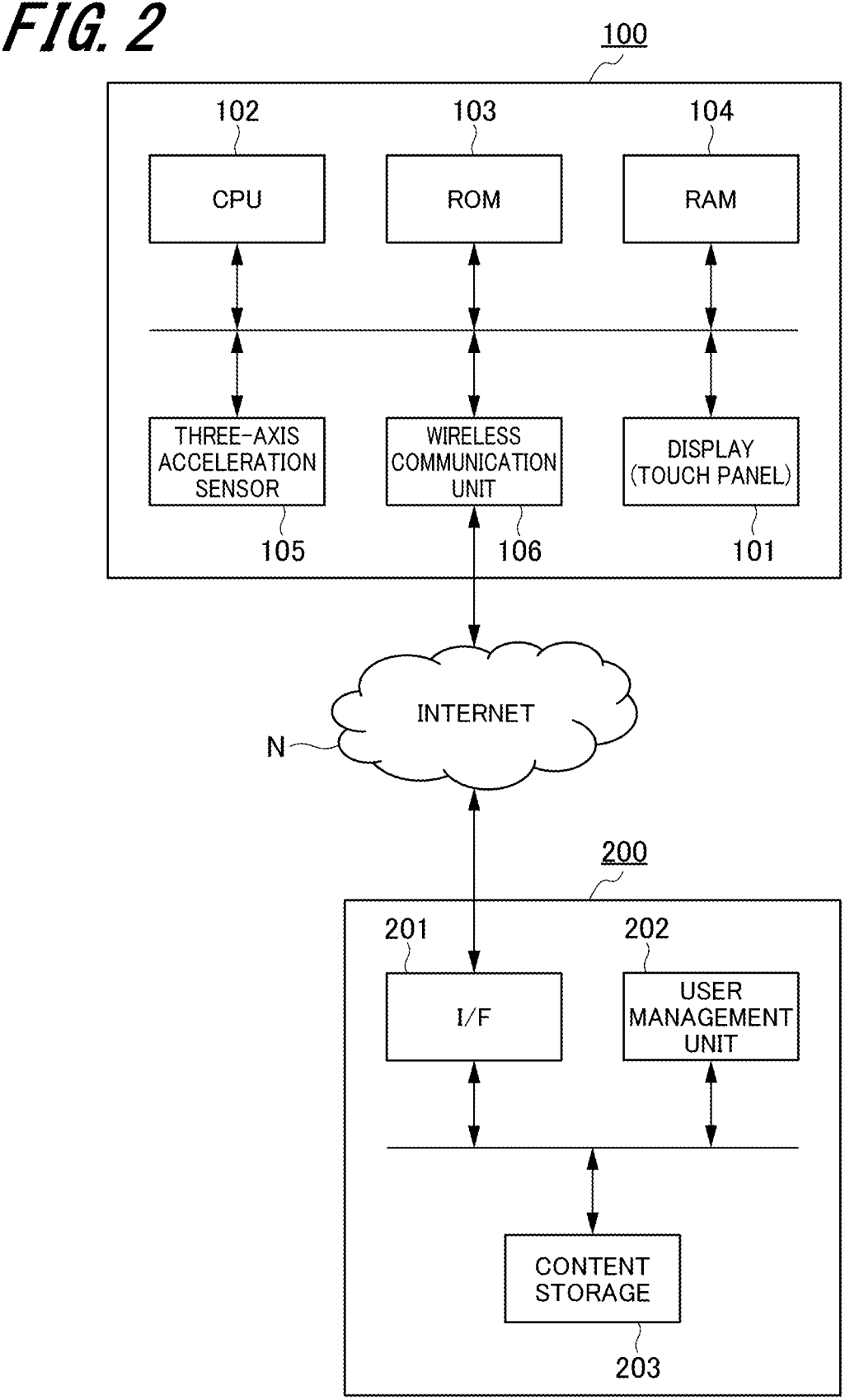
FIG. 2 is a block diagram showing a configuration example of the device according to the first embodiment of the present invention.

FIG. 2 shows an example of hardware configurations of the terminal 100 and the server 200 shown in FIG. 1.

The terminal (smartphone) 100 includes a display 101, a central processing unit (CPU) 102, a read only memory (ROM) 103, a random access memory (RAM) 104, the aforesaid three-axis acceleration sensor 105, and a wireless communication unit 106; and all these components are connected by a bus line so that data can be transferred.

An image generated in the terminal 100 or an image downloaded from the outside is displayed on the display 101. A touch panel is arranged on the display 101, and the display 101 receives an operation from the user through the touch panel.

The CPU 102 is an arithmetic processing unit that reads out the code of a program to be executed by the terminal 100 from the ROM 103 and executes the program.

The ROM 103 stores programs such as applications to be executed by the terminal 100. A program that performs psychological evaluation process to estimate the user's interest in the content being browsed is also stored in ROM 103, and such a program will be described in the present embodiment.

Variables, parameters and the like generated during the arithmetic processing are temporarily written in the RAM 104.

The three-axis acceleration sensor 105 detects the acceleration applied to the terminal 100 for each of the three orthogonal axes (x-axis, y-axis, and z-axis).

The wireless communication unit 106 is a circuit that performs wireless communication via a wireless telephone line or a wireless LAN (local area network). For example, the terminal 100 can access the server 200 through the wireless communication performed by the wireless communication unit 106 via the Internet N.

The server 200 includes a network interface 201, a user management unit 202, and a content storage 203.

The network interface 201 communicates with the terminal 100 accessed via the Internet N.

The user management unit 202 recognizes users registered for each terminal 100 accessed, and performs management processes for the recognized users. One of the management processes performed by the user management unit 202 for the users is recommending appropriate contents to the corresponding user according to, for example, the past access history of each user and preference estimated by the psychological evaluation process. The user management unit 202 acquires and holds the data of the result of psychological evaluation process performed in the accessed terminal 100.

The contents (for example, electronic comics, electronic books and/or like) to be provided by the server 200 are stored in the content storage 203. The contents stored in the content storage 203 are read out by the user management unit 202 according to an instruction from the terminal 100 that accesses the server 200, and transferred to the terminal 100.

[1-3. Examples of Configuration for Performing Psychological Evaluation Process]

Figure 3:
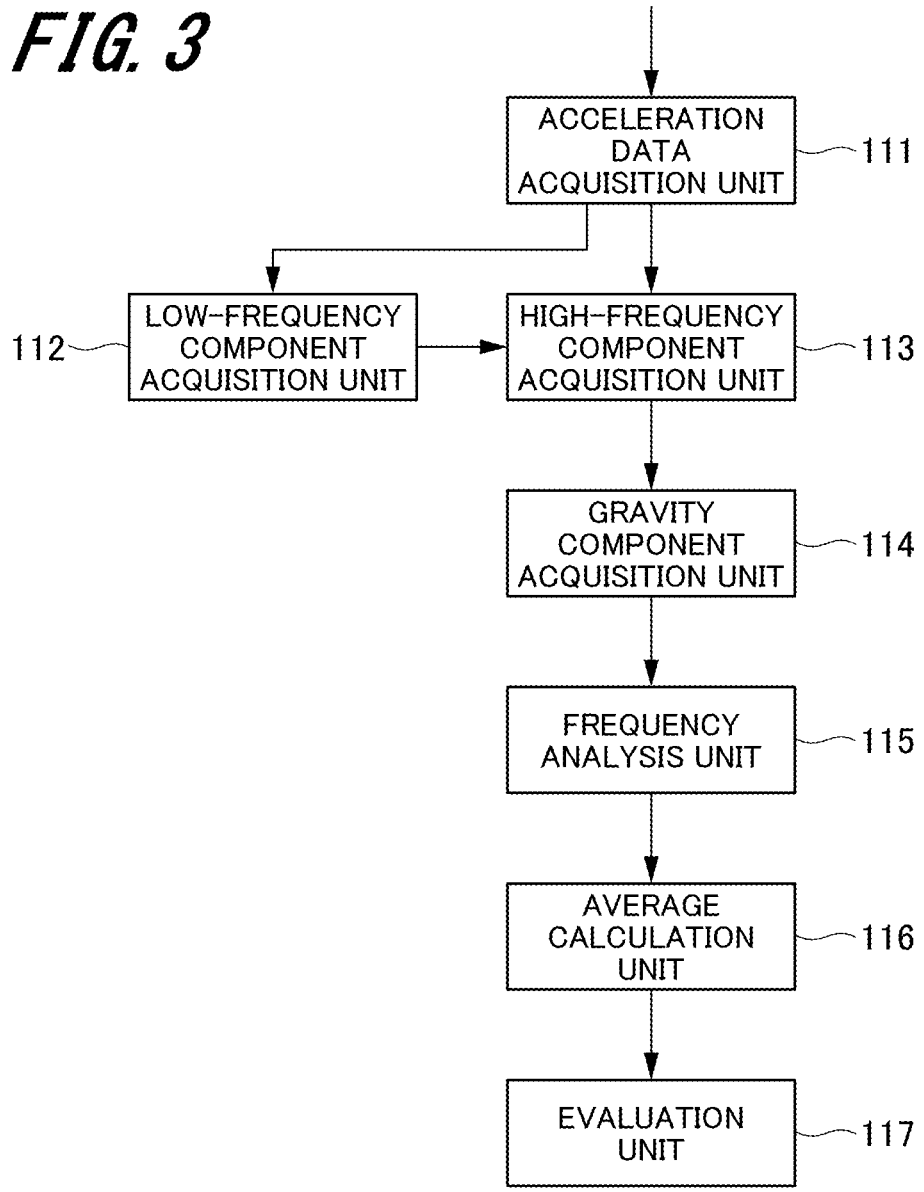
FIG. 3 is a block diagram showing a functional configuration of the psychological evaluation device according to the first embodiment of the present invention.

FIG. 3 is a functional block diagram showing a configuration in which the terminal 100 performs the psychological evaluation process. The CPU 102 of the terminal 100 shown in FIG. 2 reads out a program from the ROM 103 and executes the program to thereby obtain the configuration and function of each processing unit shown in FIG. 3.

As shown in FIG. 3, the terminal 100 includes, as the configuration for performing psychological evaluation process, an acceleration data acquisition unit 111, a low-frequency component acquisition unit 112, a high-frequency component acquisition unit 113, a gravity component acquisition unit 114, a frequency analysis unit 115, an average calculation unit 116, and an evaluation unit 117.

The acceleration data acquisition unit 111 acquires the acceleration data of three axes detected by the three-axis acceleration sensor 105 (acceleration data acquisition process). The acceleration data acquisition unit 111 samples, for example, the acceleration of the three axes outputted by the three-axis acceleration sensor 105 at a predetermined sampling frequency (for example, 50 Hz) to acquire an instantaneous value of the acceleration.

The low-frequency component acquisition unit 112 acquires low-frequency components for each of the three axes from the instantaneous value of the acceleration of the three axes obtained by the acceleration data acquisition unit 111 by using a moving average method to cut out the high-frequency components. For example, the low-frequency component acquisition unit 112 acquires low-frequency components of 1 Hz or lower by using a moving average method with a cutoff frequency of 1 Hz and a moving average point of 23 points.

The high-frequency component acquisition unit 113 subtracts the low-frequency components obtained by the low-frequency component acquisition unit 112 from the acceleration data of the three axes acquired by the acceleration data acquisition unit 111 to acquire high-frequency components with a frequency higher than the cutoff frequency (1 Hz) for each of the three axes.

The gravity component acquisition unit 114 acquires gravity components of each of the three axes and combines the acquired gravity components of the three axes (gravity component acquisition process).

The gravity components are acquired by the gravity component acquisition unit 114 by using, for example, the following [Expression 1]:

$$f_H \times (f_L/9.8) \quad\quad\quad [\text{Expression 1}]$$

Here, $f_H$ represents a high frequency component acquired by the high-frequency component acquisition unit 113, and $f_L$ represents a low-frequency component acquired by the low-frequency component acquisition unit 112. The reason for dividing the low-frequency component by 9.8 in [Expression 1] is based on the fact that the acceleration of gravity is 9.8 m/s$^2$.

Further, the gravity component acquisition unit 114 combines the gravity components $X_G$, $Y_G$, $Z_G$ of the three axes.

To be specific, the gravity component acquisition unit 114 obtains a summed value $[X_G+Y_G+Z_G]$ of the gravity components of the three axes.

Acquiring the gravity components from the acceleration data of the three axes obtained by the acceleration data acquisition unit 111 in such a manner is equivalent to decomposing the acceleration data of the three axes into a DC component (static acceleration) and an AC component (dynamic acceleration) to acquire the AC component in the gravity direction.

Figure 4:
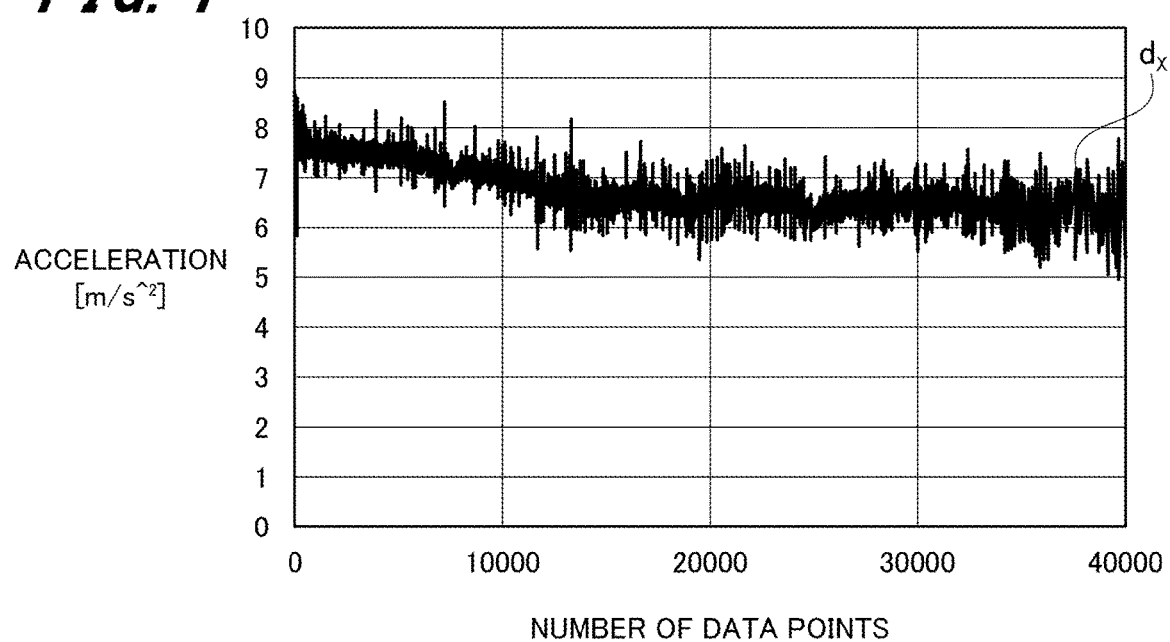
FIG. 4 is a diagram showing an example of acceleration data obtained from an acceleration sensor according to the first embodiment of the present invention.
Figure 5:
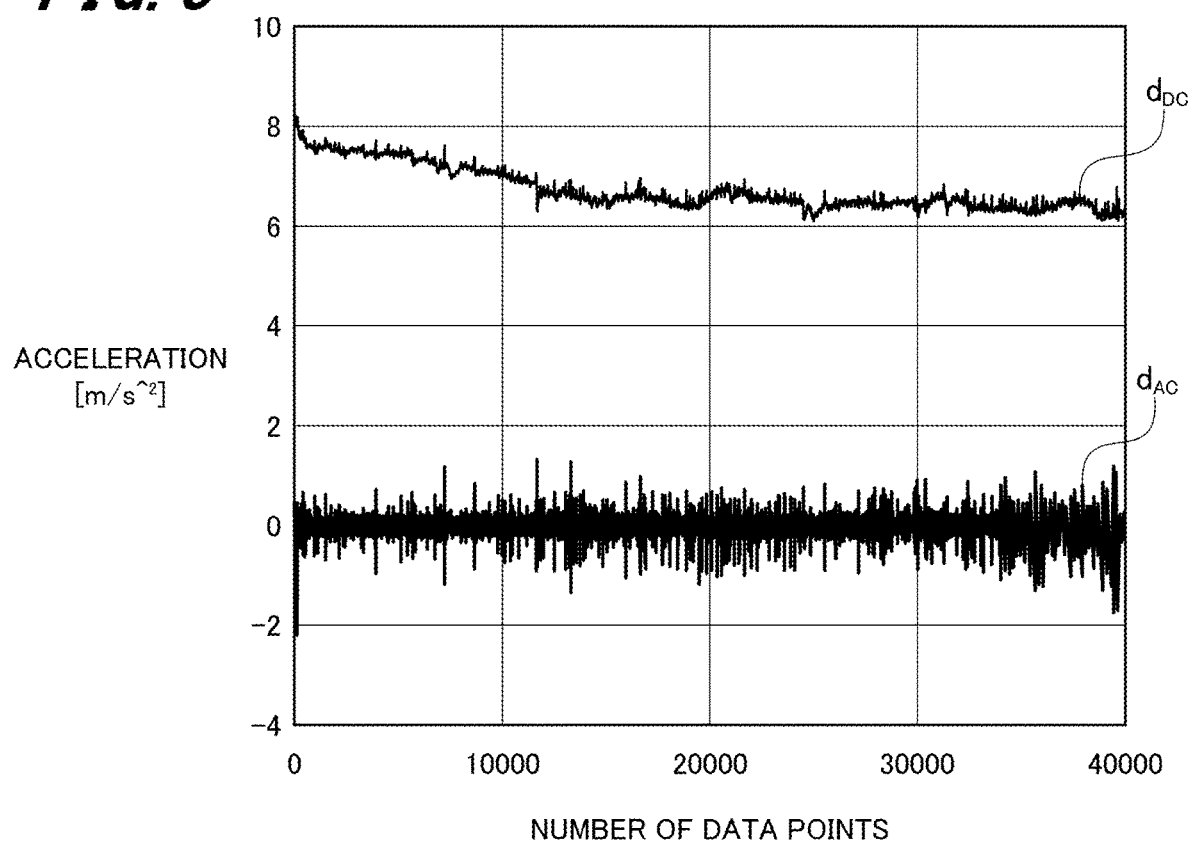
FIG. 5 is a diagram showing an example in which the acceleration data obtained from the acceleration sensor according to the first embodiment of the present invention is decomposed into a DC component and an AC component.

To be specific, an acceleration data $d_x$ detected by the three-axis acceleration sensor 105 is shown in FIG. 4 and FIG. 5, and the acceleration data $d_x$ shown in FIG. 4 can be decomposed into a DC component $d_{DC}$ and an AC component $d_{AC}$ as shown in FIG. 5. The AC component $d_{AC}$ is obtained by removing the DC component $d_{DC}$, which are the gravity component acquired by the gravity component acquisition unit 114, from the acceleration data $d_x$ detected by the three-axis acceleration sensor 105.

The DC component $d_{DC}$ corresponds to the gravitational acceleration, and the AC component $d_{AC}$ corresponds to the acceleration at which the terminal 100 moved. Here, the gravity component acquisition unit 114 acquires the AC component $d_{AC}$ in the gravity direction (vertical direction), and uses the AC component $d_{AC}$ in the gravity direction to perform an analysis process on the interest of the user as described below.

Thus, by decomposing the acceleration data of the three axes acquired by the acceleration data acquisition unit 111 into the DC component $d_{DC}$ and the AC component $d_{AC}$, the AC component corresponding to the acceleration at which the terminal 100 moved can be easily and accurately detected based on the output of the three-axis acceleration sensor 105. As can be known from the following description, the AC component corresponding to the acceleration at which the terminal 100 moved is obtained by accurately detecting the physiological tremor, which represents the physical condition of the user, and can be applied to various kinds of estimation, such as the estimation of the user's interest in the content being browsed.

Note that, there are two types of three-axis acceleration sensor 105, one is the type that ignores the DC component of 0 Hz and the other is the type that does not ignore the DC component of 0 Hz; the three-axis acceleration sensor 105 used in the terminal (smartphone) 100 according to the present embodiment is the type that does not ignore the DC component of 0 Hz.

Description is continued below with reference back to FIG. 3. The frequency analysis unit 115 performs frequency analysis by conducting a fast Fourier transform on the summed value $[X_G+Y_G+Z_G]$ of the gravity components of the three axes, to thereby acquire the components for each frequency (frequency analysis process). Here, the frequency analysis unit 115 performs the Fast Fourier Transform with 512 calculation points, for example. The frequency analysis result of the AC component $d_{AC}$ of the acceleration data is obtained by performing the frequency analysis by conducting the fast Fourier transform to obtain the analysis result of the high frequency component corresponding to the AC component $d_{AC}$ in the gravity direction (vertical direction).

The average calculation unit 116 acquires an average value of the results of the frequency analysis obtained by the frequency analysis unit 115 for a predetermined time for each frequency (average calculation process). Here, the average calculation unit 116 performs a process of acquiring an ensemble average to acquire an average value for each predetermined time while overlapping the average value by 50%.

The evaluation unit 117 integrates the component of the frequency of a first peak (the frequency at which the highest peak is obtained) between 2 Hz and 5 Hz with respect to the average value obtained by the average calculation unit 116, for a fixed period (for example, the period while the content is being browsed), and estimates the interest of the user in the content being browsed based on the integrated value (evaluation process).

[1-4. Examples of the Flow of the Psychological Evaluation Process]

Figure 6:
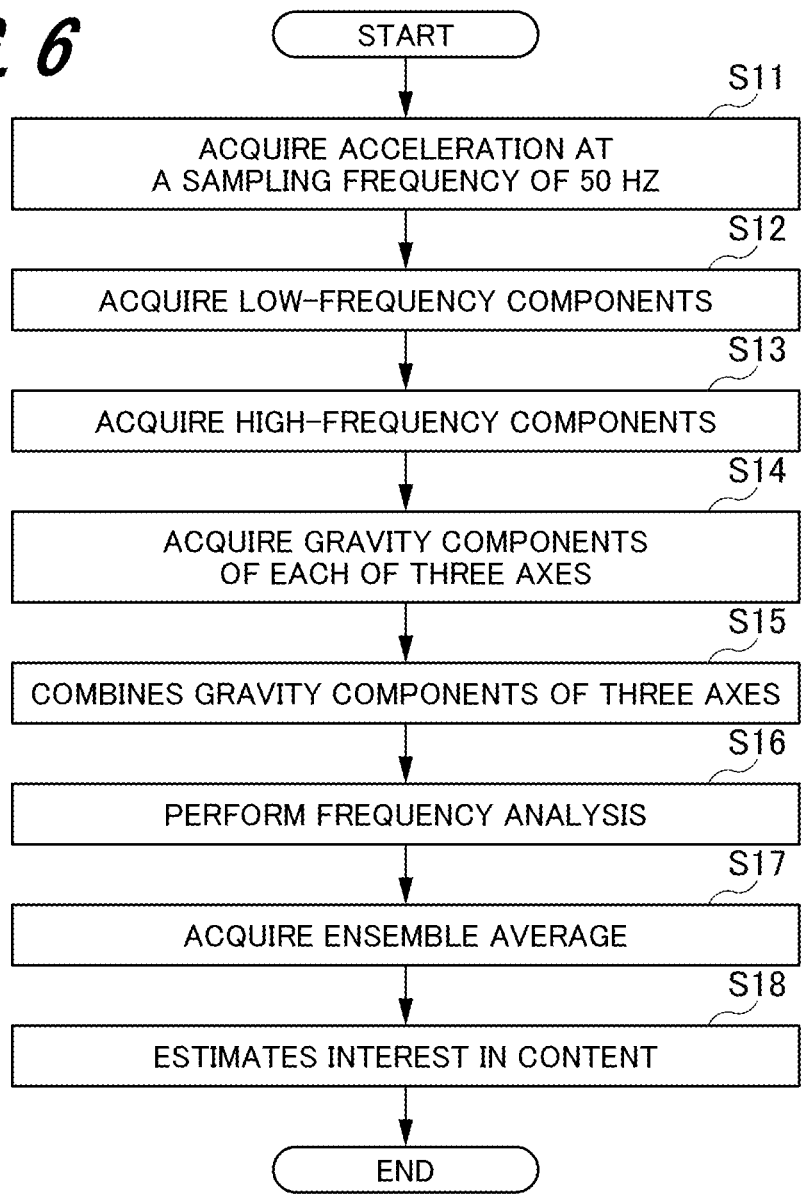
FIG. 6 is a flowchart showing the flow of a psychological evaluation process according to the first embodiment of the present invention.

FIG. 6 is a flowchart showing a flow in which the terminal 100 performs the psychological evaluation process.

The psychological evaluation process shown in the flowchart of FIG. 6 is executed by each of the processing units shown in FIG. 3.

First, the acceleration data acquisition unit 111 samples the acceleration data of the three axes detected by the three-axis acceleration sensor 105 at a predetermined sampling frequency (for example, 50 Hz) to acquire the acceleration data (Step S11).

Next, the low-frequency component acquisition unit 112 acquires the low-frequency components of a predetermined frequency or lower (for example, 1 Hz or lower) for each of the three axes from the acceleration of the three axes acquired by the acceleration data acquisition unit 111 (step S12). Further, the high-frequency component acquisition unit 113 subtracts the low-frequency components obtained by the low-frequency component acquisition unit 112 from the acceleration data of the three axes obtained by the acceleration data acquisition unit 111 to acquire the high-frequency components with a frequency higher than the cutoff frequency (1 Hz) for each of the three axes (step S13).

Thereafter, the gravity component acquisition unit 114 acquires the gravity components of each of the three axes (step S14), and combines the acquired gravity components of the three axes (step S15).

Further, the frequency analysis unit 115 performs frequency analysis by conducting a fast Fourier transform on the combined value of the gravity components of the three axes (the summed value $[X_G+Y_G+Z_G]$ obtained by the [Expression 1]) (step S16).

Further, the average calculation unit 116 acquires an average value of the results of the frequency analysis obtained by the frequency analysis unit 115 for a predetermined time for each frequency (50% overlapped ensemble average) (step S17).

Further, the evaluation unit 117 integrates the frequency of the first peak between 2 and 5 Hz for a fixed period with respect to the average value obtained by the average calculation unit 116, and estimates the interest of the user in the content being browsed based on the integrated value (step S18).

Incidentally, examples of concrete evaluation of the interest estimation process for estimating user's interest according to the present embodiment will be described while comparing each embodiment, after the description of a second embodiment to be described later.

2. Second Embodiment

A second embodiment according to the present invention will be described below with reference to FIG. 7 to FIG. 9.

Figure 7:
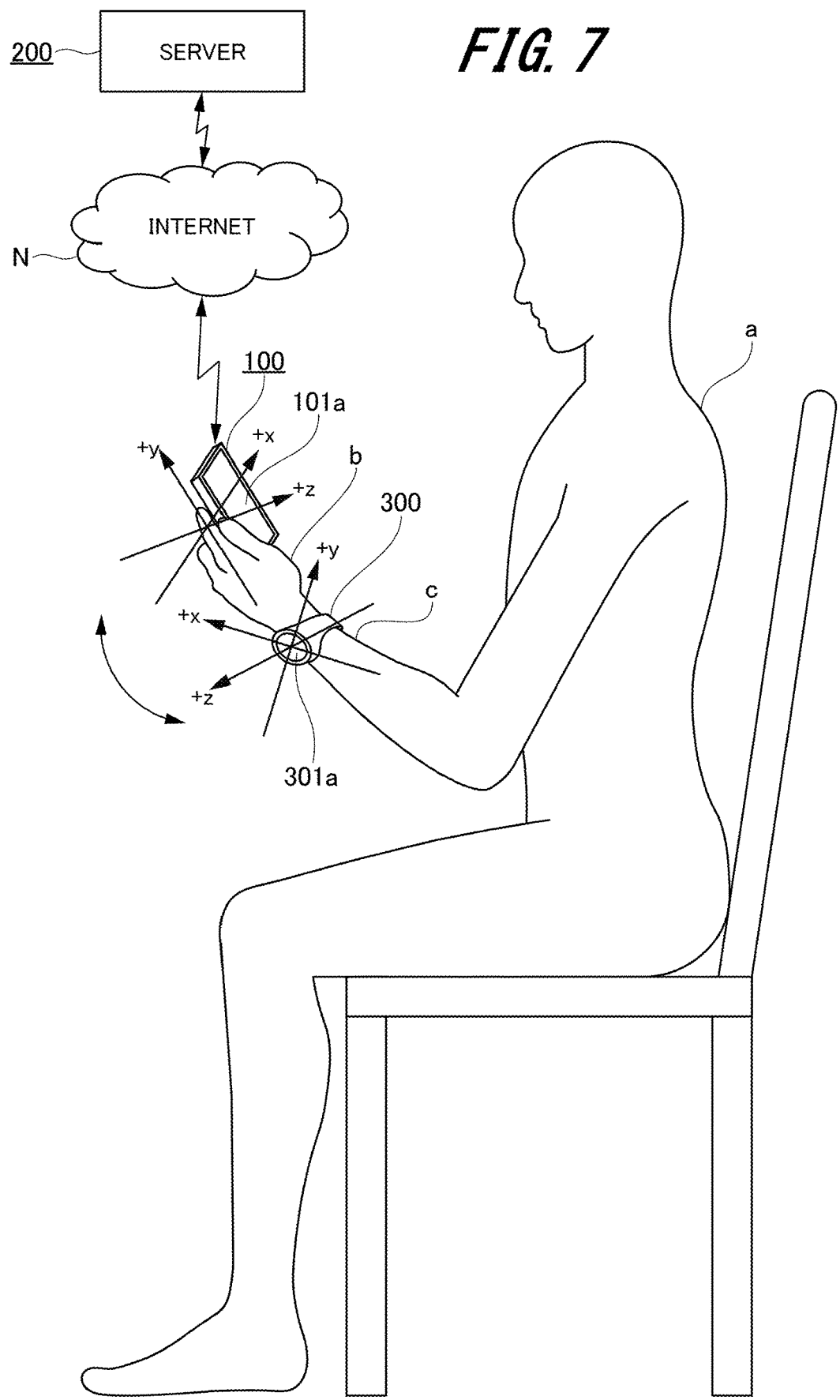
FIG. 7 is a view showing an application example of a psychological evaluation device according to a second embodiment of the present invention.
Figure 8:
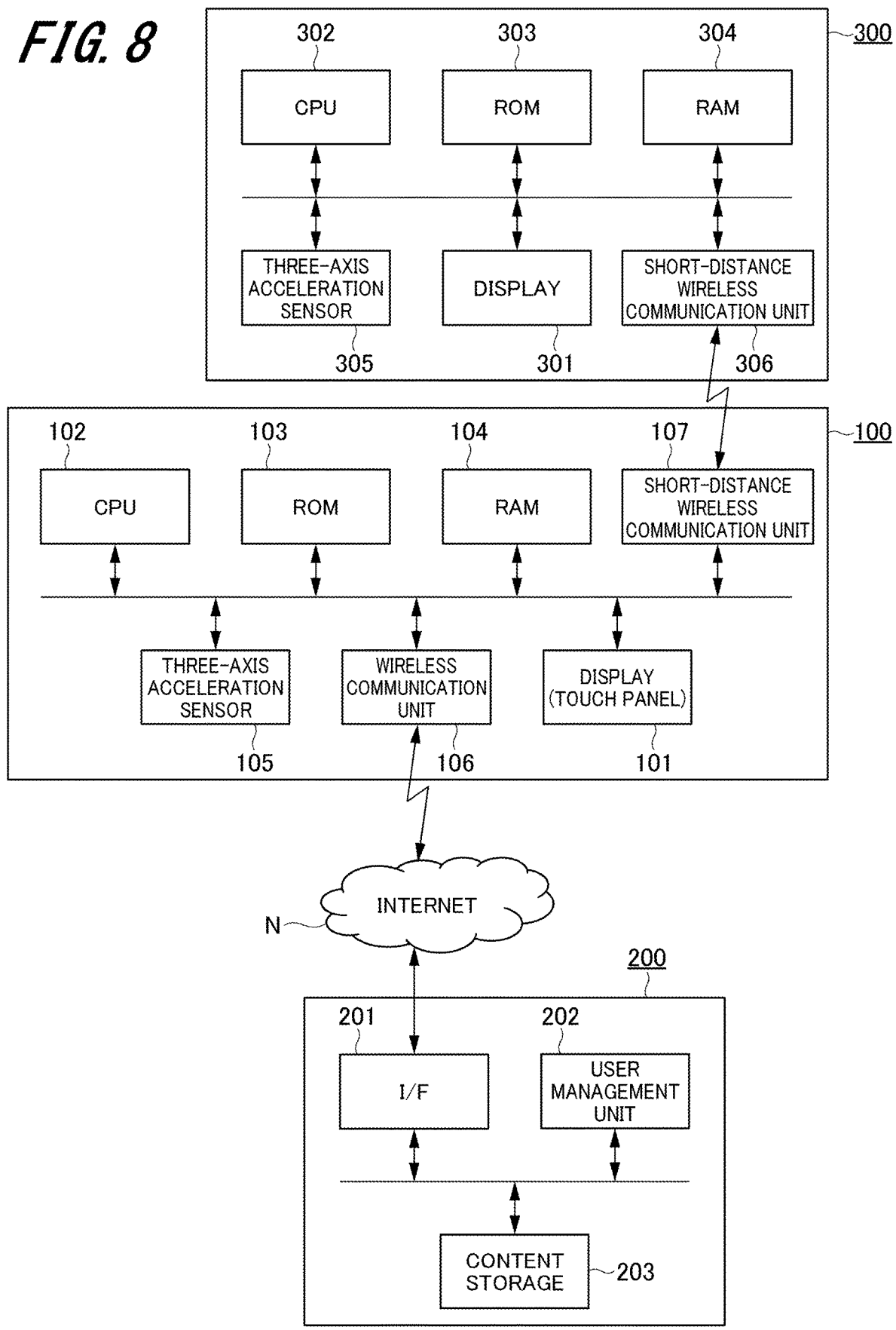
FIG. 8 is a block diagram showing a configuration example of the device according to the second embodiment of the present invention.
Figure 9:
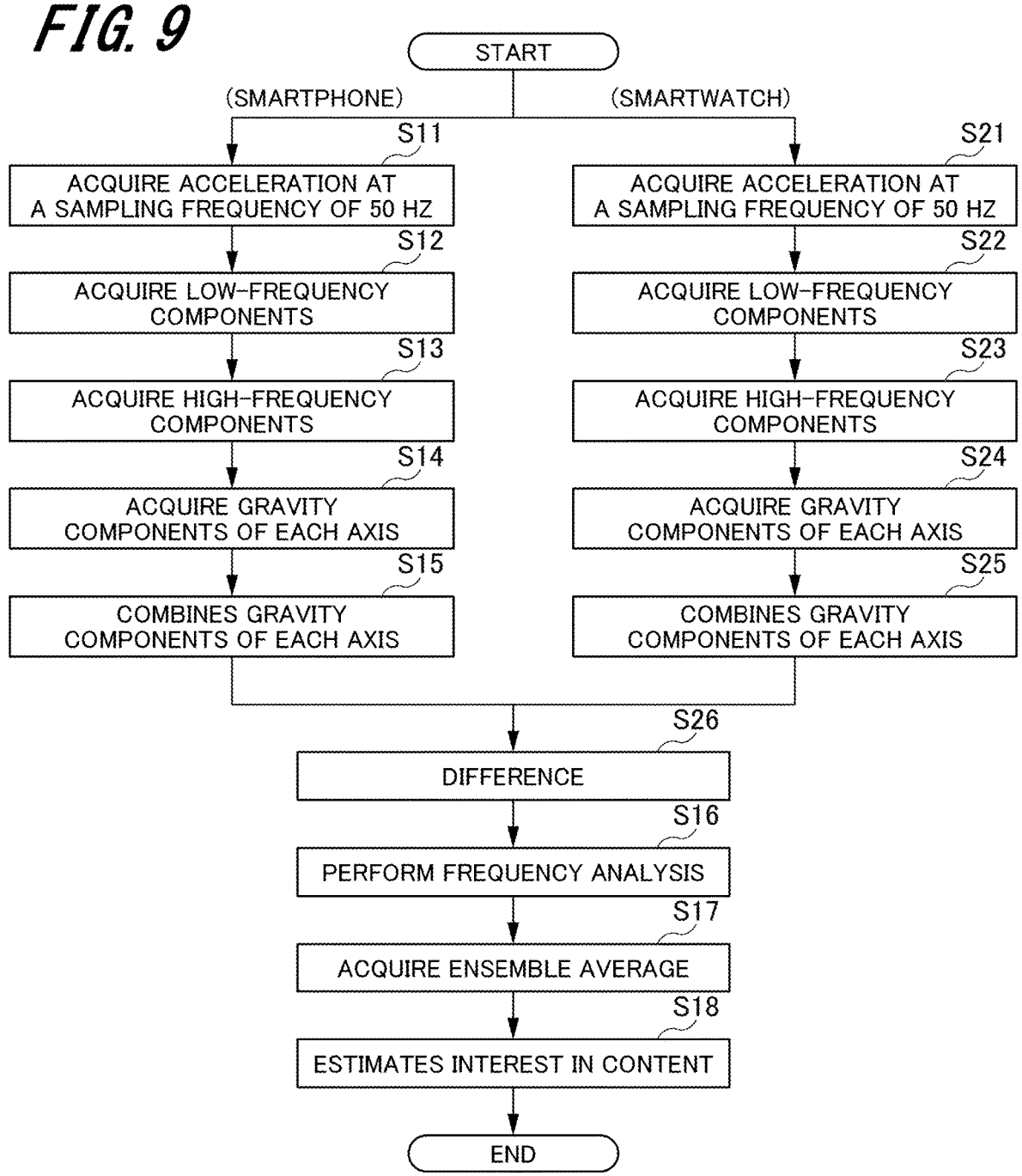
FIG. 9 is a flowchart showing the flow of a psychological evaluation process according to the second embodiment of the present invention.

Note that, in FIG. 7 to FIG. 9, the same components as those of FIG. 1 to FIG. 6, which have been described in the first embodiment, are denoted by the same numerals, and the explanation thereof will not be repeated.

[2-1. Application Examples of Psychological Evaluation Device]

FIG. 7 is a view showing an application example of a psychological evaluation device according to the second embodiment.

In the second embodiment, similar to the first embodiment, a content (an electronic comic or the like) is displayed on the terminal 100 (smartphone) held by a user (subject) with one hand, and the terminal 100 or the server 200 performs the psychological evaluation for estimating the interest of the user in the contents being browsed.

Further, the second embodiment is also similar to the first embodiment in that the terminal 100 communicates with the server 200 via the Internet N, and the content delivered from the server 200 is displayed on the screen 101a of the display 101 of the terminal 100.

In the second embodiment, as shown in FIG. 67, an auxiliary terminal 300 called smartwatch is worn on an arm c of the user. Here, the arm c is the arm on the side that holds the terminal 100. The auxiliary terminal (smartwatch) 300 is similar in shape to a wristwatch, and various information is displayed on a screen 301a of a display 301 of the auxiliary terminal 300.

Specifically, the auxiliary terminal 300 has various sensors built therein for measuring the user's condition such as pulse rate and the like, and the measured pulse rate and the like are displayed on the screen 301a. Further, the auxiliary terminal 300 has a function for performing short-distance wireless communication with the terminal 100, and can notify incoming telephone call or e-mail of the terminal 100. Further, a three-axis acceleration sensor 305 (see FIG. 8) is built in the auxiliary terminal 300.

The terminal 100 detects a vibration, referred to as physiological tremor, of a hand b of a user a using the 3-axis acceleration sensor 105 built in the terminal 100 and the 3-axis acceleration sensor 305 built in the auxiliary terminal 300. The terminal 100 estimates the user's interest in the content based on the vibration state of the user who is browsing the content (psychological evaluation).

As shown in FIG. 7, the coordinate axes (x-axis, y-axis, and z-axis) of the three axes detected by the three-axis acceleration sensor 105 built in the terminal 100 and the coordinate axes (x-axis, y-axis, and z-axis) of the three axes detected by the three-axis acceleration sensor 305 built in the auxiliary terminal 300 are local coordinate axes corresponding to the orientation of the terminal 100 and the orientation of the 300, respectively, and they do not match each other.

[2-2. Examples of Device Configuration]

FIG. 8 shows an example of the hardware configurations of the terminal 100, the server 200 and the auxiliary terminal 300 shown in FIG. 7.

The configurations of the terminal (smartphone) 100 and the server 200 are basically the same as those shown in FIG. 2 in the first embodiment. However, the terminal 100 of the second embodiment is different from the terminal 100 shown in FIG. 2 in that the terminal 100 of the second embodiment is provided with a short-distance wireless communication unit 107 for performing communication with the auxiliary terminal 300.

The auxiliary terminal (smartwatch) 300 includes a display 301, a CPU 302, a ROM 303, a RAM 304, a three-axis acceleration sensor 305, and a short-distance wireless communication unit 306, and all these components are connected by a bus line so that data can be transferred.

An image containing a message and the like generated in the auxiliary terminal 300 is displayed on the display 301.

The CPU 302 is an arithmetic processing unit that reads out the code of a program to be executed by the auxiliary terminal 300 from the ROM 303 and executes the program.

The ROM 303 stores programs such as applications to be executed by the auxiliary terminal 300.

Variables, parameters and the like generated during the arithmetic processing are temporarily written in the RAM 304.

The three-axis acceleration sensor 305 detects acceleration applied to the auxiliary terminal 300 for each of the three orthogonal axes (x-axis, y-axis, and z-axis).

The short-distance wireless communication unit 306 performs wireless communication with the terminal 100. The short-distance wireless communication unit 306 performs the wireless communication with the short-distance wireless communication unit 107 provided on the side of the terminal 100 using a short-distance wireless communication standard called Bluetooth (registered trademark), for example.

[2-3. Examples of Flow of Psychological Evaluation Process]

FIG. 9 is a flowchart showing a flow in which the terminal (smartphone) 100 and the auxiliary terminal (smartwatch) 300 are used to perform the psychological evaluation process.

Note that, in FIG. 9, the processes shown in steps S11 to S18 are the same as those performed in the terminal 100, and have been described with reference to FIG. 6 of the first embodiment, so that the explanation of these processes will not be repeated.

In the auxiliary terminal 300, the CPU 302 executes a program prepared in the ROM 303 to thereby sample the acceleration data of the three axes detected by the three-axis acceleration sensor 305 at a predetermined sampling frequency (for example, 50 Hz) to acquire the acceleration of the three axes (step S21). Further, from the acceleration of the three axes acquired by the three-axis acceleration sensor 305, the auxiliary terminal 300 acquires, under the control of the CPU 302, the low-frequency components of a predetermined frequency or lower (for example, 1 Hz or lower) for each of the three axes (step S22) and acquires the high-frequency components higher than a cutoff frequency (1 Hz) for each of the three axes (step S23).

Further, the auxiliary terminal 300 acquires, under the control of the CPU 302, the gravity components of each of the three axes from the high-frequency components of the acceleration of the three axes (step S24), and combines the acquired gravity components of the three axes (step S25). The combined value (i.e., the summed value) of the gravity components obtained in the step S25 is transmitted from the short-distance wireless communication unit 306 to the terminal 100.

In the terminal 100, the combined value of the gravity components of the three axes transmitted from the auxiliary terminal 300 is received by the short-distance wireless communication unit 107, and a difference between the combined value of the gravity components of the three axes on the side of the terminal 100 calculated in the step S15 and the combined value of the gravity components of the three axes obtained in the step S25 is calculated (step S26). The calculation of the difference is performed by, for example, the gravity component acquisition unit 114 of the terminal 100 shown in FIG. 3.

Further, the difference of the combined values of the gravity components of the three axes between the terminal 100 and the auxiliary terminal 300 obtained in the step S26 is transmitted to the frequency analysis unit 115 where frequency analysis is performed by conducting a fast Fourier transform on the difference of the combined values of the gravity components of the three axes (step S16). Hereinafter, similar to the processes in the flowchart of FIG. 6, the average calculation unit 116 and the evaluation unit 117 perform the process of step S17 and the process of step S18.

3. Examples of Evaluation According to First and Second Embodiments

Concrete examples and effects of the evaluation process for estimating the user's interest in the content being browsed according to the aforesaid first and second embodiments will be described below.

Figure 10:
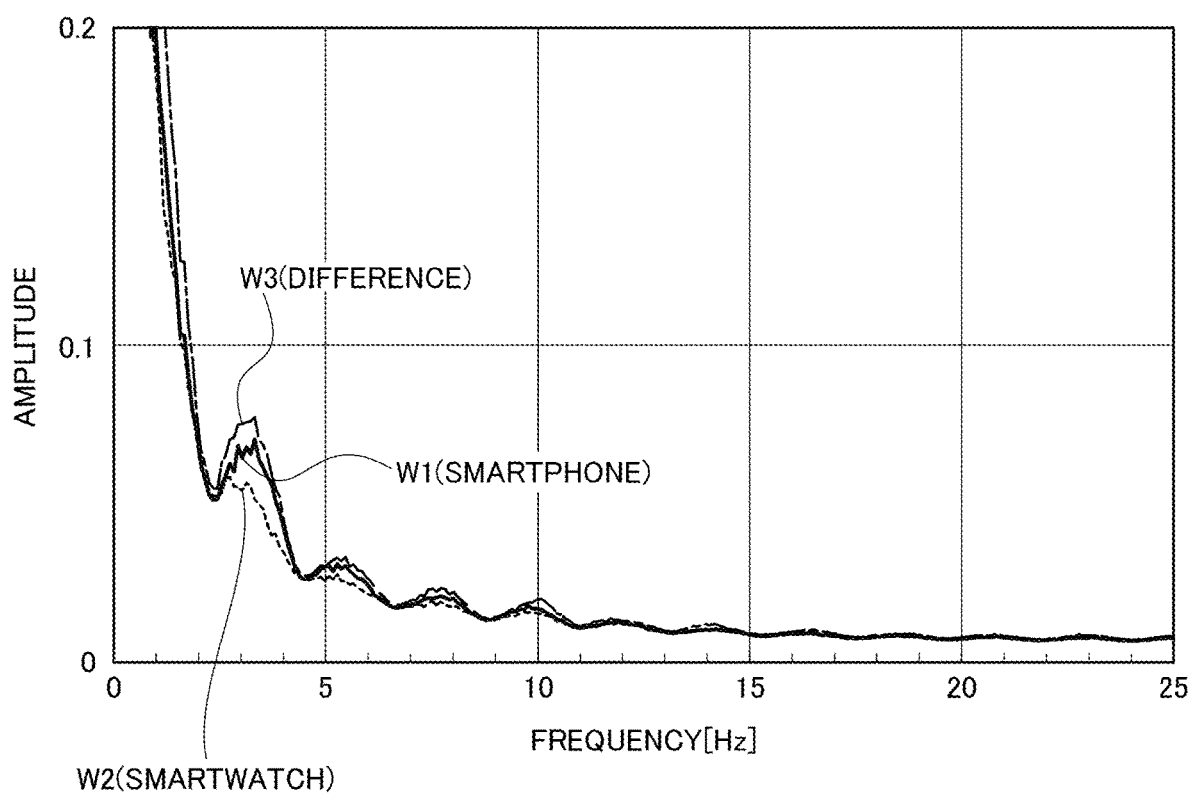
FIG. 10 is a graph showing an example of amplitudes for each frequency when browsing a content measured by applying the first and second embodiments of the present invention.

FIG. 10 is a graph showing amplitudes of the vertical component (component in the gravity direction) with respect to the frequency of the acceleration data of the terminal (smartphone) 100, which is generated when the user is browsing the content (which is electronic comics here) with the terminal.

In FIG. 10, the horizontal axis represents frequency, and the vertical axis represents amplitude of acceleration; the horizontal axis indicates a frequency range from 1 Hz to 25 Hz. The amplitude is an integral value of the average of the acceleration data generated when the user is browsing the content. A characteristic W1 shown in FIG. 10 represents the amplitude of each frequency caused by the acceleration data detected by the three-axis acceleration sensor 105 of the terminal (smartphone) 100. The characteristic W1 corresponds to the value calculated in the first embodiment.

A characteristic W2 represents the amplitude of each frequency caused by the acceleration data detected by the three-axis acceleration sensor 305 of the auxiliary terminal (smartwatch) 300, and a characteristic W3 represents the amplitude of each frequency caused by difference data between the output of three-axis acceleration sensor 105 of the terminal 100 and the output of three-axis acceleration sensor 305 of the auxiliary terminal 300. The characteristic W3 corresponds to the value calculated in the second embodiment.

Note that, since the difference data shown in FIG. 10 is obtained by analyzing a difference of frequency signals, the amplitude W3 of the difference may be larger than the amplitudes W1 and W2 of the original signals, depending on the phase of each acceleration data.

As can be known from the characteristics W1, W2, and W3 in FIG. 10, in a band lower than 2 Hz, amplitudes are very large due to the movement of the hand and/or the arm that hold the terminal 100; however, in a band from 2 Hz to 5 Hz, reasonable amplitudes having peaks at about 3 Hz are detected. In particular, the amplitude characteristic W1 caused by the output of the three-axis acceleration sensor 105 of the terminal 100 and the amplitude characteristic W3 of the difference are both a ridge-like characteristic where a clear peak is detected.

In a band higher than 5 Hz, the detected amplitude is smaller than in the band from 2 Hz to 5 Hz, and the detected amplitude value is very small.

In the amplitude characteristics shown in FIG. 10, the amplitude detected in the band from 2 Hz to 5 Hz corresponds to the component of vibration caused by the physiological tremor of the user. The physiological tremor of the user is a vibration caused by repeated contraction and relaxation of muscles of the user, and healthy people are usually not aware of the vibration caused by the physiological tremor. The frequency of the vibration caused by the physiological tremor varies depending on the part of the body; for example, it is known that the physiological tremor of fingers has major frequencies in a range between 10 Hz and 25 Hz. However, these frequencies are obtained in the state where the fingers do not hold anything.

It is known that the vibration state caused by the physiological tremor of the user varies according to the interest of the user.

To be specific, it is known that when a user browses a content such as electronic comics displayed on the terminal 100 while holding the terminal 100 with his (or her) hand, the vibration of the hand caused by physiological tremor decreases if the user is interested in the content (i.e., if the user thinks that the content is interesting), and the vibration of the hand caused by physiological tremor increases if the user is not interested in the content (i.e., if the user thinks that the content is not interesting).

The peak values of the amplitudes of the characteristic W1 based on the output of the three-axis acceleration sensor 105 of the terminal 100 and the characteristic W3 based on the difference data between the terminal 100 and the auxiliary terminal 300, detected in the band from 2 Hz to 5 Hz, are obtained by detecting the component of the vibration of the hand caused by the physiological tremor, and vary to reflect the user's interest in the content having been browsed. In the evaluation process for evaluating the interest in the content as shown in step S18 of the flowcharts of FIG. 6 and FIG. 9, when the peak value of the amplitude is low, the interest in the browsed content is estimated to be high, and when the peak value of the amplitude is high, the interest in the browsed content is estimated to be low.

FIG. 11 shows an example of the correlation between interestingness of a certain content and amplitude integral values of each frequency band when the user browsed the content.

FIG. 11 shows average and variance of the amplitude integral values of the output of the three-axis acceleration sensor 105 of the terminal (smartphone) 100 and average and variance of the amplitude integral values of the output of the difference between the terminal 100 and the auxiliary terminal 300 for four frequency bands which are 1 Hz to 2 Hz, 2 Hz to 3 Hz, 3 Hz to 4 Hz, and 4 Hz to 5 Hz.

In the case where the amplitude integral value is detected by the terminal 100 alone, since the average of the amplitude integral values in the band from 3 Hz to 4 Hz is the highest value, the interest evaluation process can be performed using the average and variance of the amplitude integral values in the band from 3 Hz to 4 Hz.

In the case where the amplitude integral value is obtained based on the output of the difference between the terminal 100 and the auxiliary terminal 300, since the average of the amplitude integral values in the band from 2 Hz to 3 Hz is the highest value, the interest evaluation process can be performed using the average and variance of the amplitude integral values in the band from 2 Hz to 3 Hz in the case where the difference output is used.

Figures 12, 13:
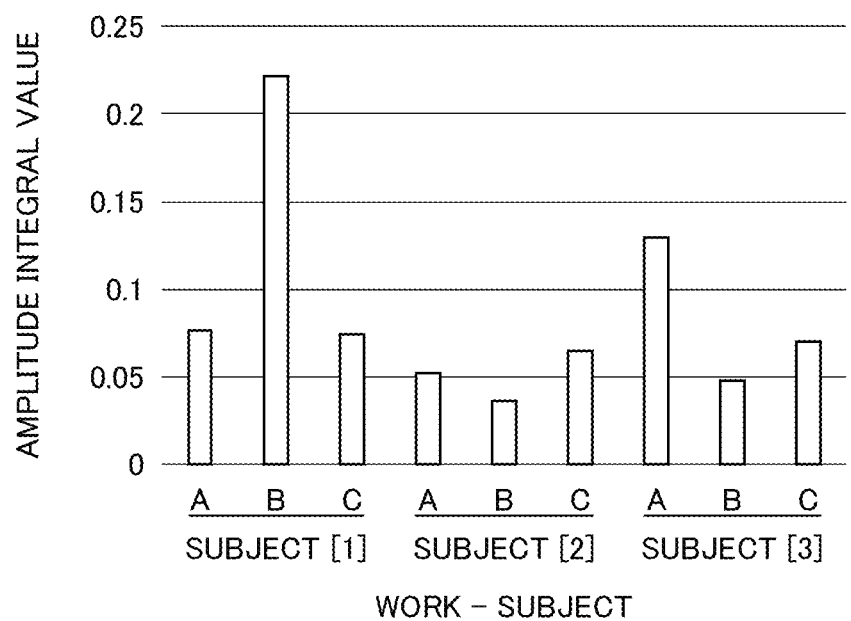
FIG. 12 is a graph showing an example of amplitude integral values in a range of 2.5 Hz to 3.5 Hz measured by applying the second embodiment of the present invention.
FIG. 13 is a table showing an example of questionnaire evaluation values when performing measurement by applying the second embodiment of the present invention.

FIG. 12 shows amplitude integral values of three works A, B, and C obtained when the works are being browsed by three subjects [1], [2], and [3] for a fixed period of time on the terminal 100. FIG. 13 shows results of questionnaires conducted by the three subjects [1], [2], and [3] after they have browsed the works A, B, and C on the terminal 100 for the fixed period of time. The results of the questionnaires show an example in which whether or not each work A, B and C was interesting was evaluated on a scale of 1 to 10 (the value 10 represents the highest evaluation, and the value 1 represents the lowest evaluation).

The amplitude integral values shown in FIG. 12 are the amplitude integral values of the output of the difference between terminal 100 and auxiliary terminal 300.

In the case of the subject [1], as shown in FIG. 12, the amplitude integral values of the work A and work C are relatively low, and the amplitude integral value of the work B is higher than the amplitude integral values of the work A and work C. On the other hand, in the results of the questionnaires shown in FIG. 13, the work B has the lowest evaluation value of "5", the work A has an evaluation value of "6" which is higher than the work B, and the work C has a further higher evaluation value of "7". Therefore, it can be known that the amplitude integral values almost reflect the interests of the subject [1] in the works A, B, and C.

In the case of subject [2], as shown in FIG. 12, the amplitude integral values of the works A, B and C are almost the same. On the other hand, in the results of the questionnaires shown in FIG. 13, the evaluation value of the work A is "7", the evaluation value of the work B is "8", and the evaluation value of the work C is "7"; which means that there is little change in the interests of the three works. Therefore, it can be known that, in the case of the subject [2], the amplitude integral values also almost reflect the interests in the works A, B, and C.

In the case of the subject [3], as shown in FIG. 12, the amplitude integral value of the work A is relatively high, and the amplitude integral values of the work B and work C are lower than the work A. On the other hand, in the results of the questionnaires shown in FIG. 13, the work A has the lowest evaluation value of "4", the work B has an evaluation value of "7" which is higher than the work A, and the work C has a further higher evaluation value of "9". Therefore, it can be known that, in the case of the subject [3], the amplitude integral values also almost reflect the interests in the works A, B, and C.

Thus, there is a clear correlation between the interest in the work (content) and the amplitude integral value.

In the example of FIG. 12, the amplitude integral values are obtained according to the second embodiment; however, in the case where the amplitude integral values are the amplitude integral values measured by the terminal (smartphone) 100 alone as shown in FIG. 1, there also is a peak at around 3 Hz, so that the interest in the work can be estimated based on the peak component in the same manner.

Thus, according to the first and second embodiments of the present invention, when the user displays some kind of content (such as electronic comics, electronic books, electronic magazines, videos or the like) on a terminal 100 held by his (or her) hand and browses the content, the integral value of the vibration component corresponding to the physiological tremor is obtained based on the acceleration data detected by the acceleration sensor when the content is being browsed by the user, and therefore the interest of the user in the content can be estimated from the integrated value.

Therefore, for example, by transmitting the estimated value of the interest obtained by the terminal 100 to the side of the distributor who distributes the content, the distributor can grasp the tendency of the content that the user who possesses the terminal 100 is interested in, and therefore can recommend each user the contents he (or she) is interested in.

In such a case, in the first and second embodiments of the present invention, since the AC component in the gravity direction is extracted from the output of the three-axis acceleration sensor built in the terminal 100 and the AC component is frequency-analyzed, the interest can be satisfactorily estimated regardless of the state of the hand that holds the terminal 100 (i.e., without specially fixing the hand for determining interest), and therefore the interest can be easily estimated when the user browses the contents in the way of normal daily life.

In the case of the second embodiment, the terminal (smartphone) 100 and the auxiliary terminal (smartwatch) 300 are used, and a frequency analysis is performed on the difference between the outputs of the three-axis acceleration sensor built in the terminal (smartphone) 100 and the three-axis acceleration sensor built in the auxiliary terminal (smartwatch) 300; therefore, by removing the components of vibration of the arm from the amplitude integral value, it becomes possible to estimate the interest with higher accuracy. However, as having been described above with reference to FIG. 12 and FIG. 13, it is also possible to estimate the interest from the calculated value in the first embodiment in which only the terminal (smartphone) 100 is used, so that the auxiliary terminal (smart watch) 300 is not necessarily required.

4. Third Embodiment

Next, a third embodiment according to the present invention will be described below with reference to FIG. 14 to FIG. 17.

In the first and second embodiments described above, terminals 100 and auxiliary terminals 300 possessed by a plurality of users are used to estimate a user who has high interest in a content. In contrast, in the third embodiment of the present invention, a frequency analysis is performed based on the outputs of the three-axis acceleration sensors built in both the terminal 100 and the auxiliary terminal 300 possessed by one user to thereby estimate whether or not the user who possesses the terminals has interest in a content.

Similar to the second embodiment of the present invention, in the third embodiment of the present invention, the terminal (smartphone) 100 and the auxiliary terminal (smartwatch) 300 are used to perform a frequency analysis on the difference between the outputs of the two three-axis acceleration sensors built in the two terminals. The process of performing the frequency analysis on the difference between the outputs of the three-axis acceleration sensors is the same as the process having been described in the second embodiment. The third embodiment of the present invention differs from the second embodiment in the process of evaluating the obtained frequency analysis result.

Figure 14:
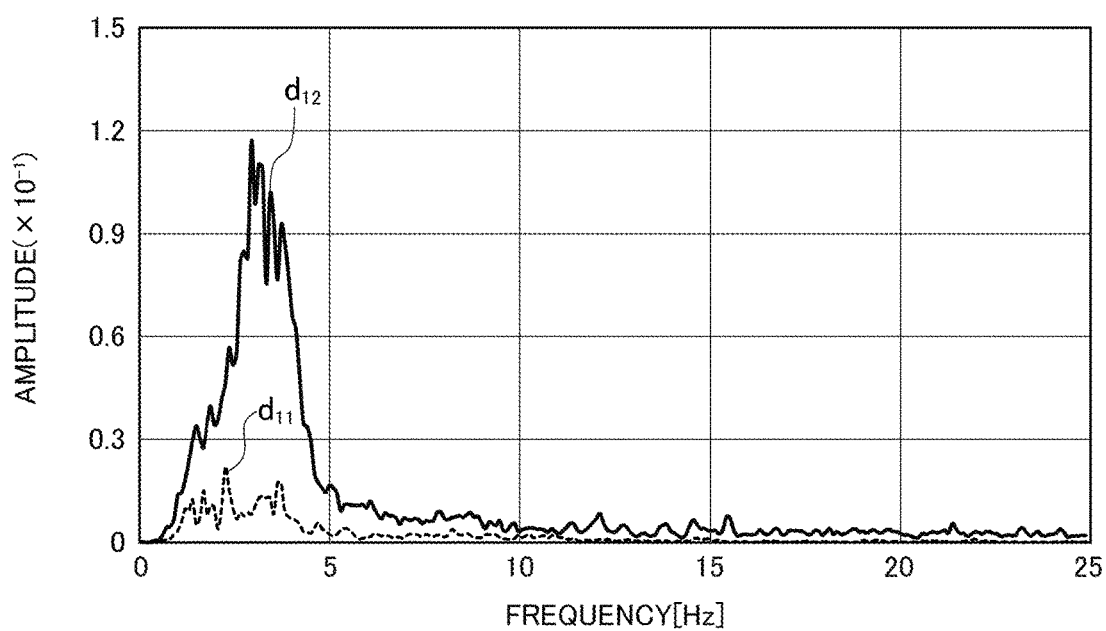
FIG. 14 is a graph showing a comparison between a frequency analysis result obtained when content is being browsed and a frequency analysis result obtained when content is not being browsed, according to a third embodiment of the present invention.

FIG. 14 shows a comparison, in the third embodiment, between a frequency analysis result ($d_{12}$) obtained when a user displays a specific content that he (or she) is interested in on a terminal 100 held by him (or her) and a frequency analysis result ($d_{11}$) obtained when a content that is other than the specific content, and that he (or she) is not interested in.

Figure 15:
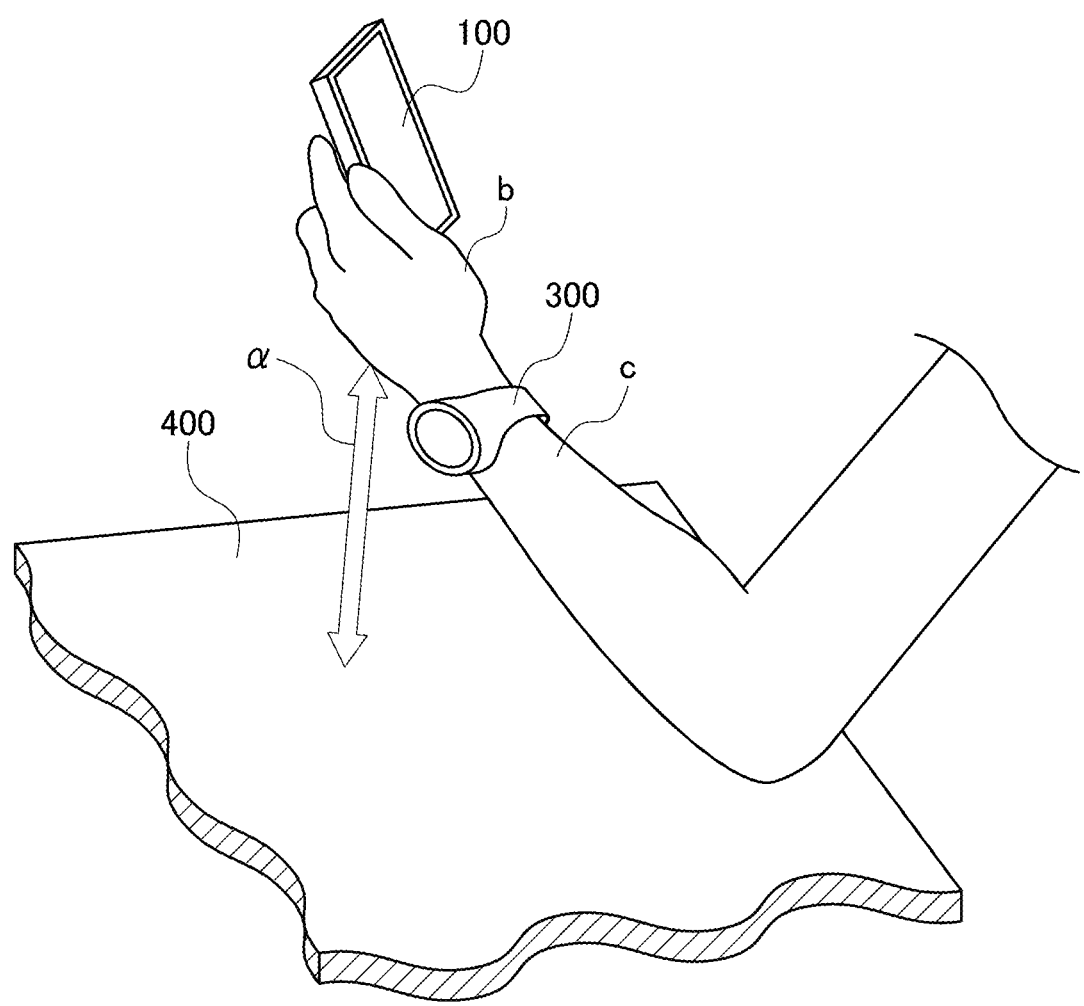
FIG. 15 is a view showing an example of the posture of the user when performing measurement according to the third embodiment of the present invention.

The frequency analysis results are measured when the user is in a state as shown in FIG. 15. To be specific, the user browses the content with the terminal (smartphone) 100 in a state in which he (or she) holds the terminal 100 by his (or her) hand b in a sitting state, while wearing the auxiliary terminal (smartwatch) 300 on his (or her) arm c, and placing the elbow of his (or her) arm c on a desk 400. When the user browses the content in the posture shown in FIG. 15, vibrations corresponding to variation in distance a between the desk 400 and the hand b are generated in the terminal 100 and the auxiliary terminal 300 mainly with the elbow placed on the desk 400 as a fulcrum. In the frequency analysis results shown in FIG. 14, large amplitude values appear in a frequency band of about 3 Hz to 5 Hz.

The frequency analysis results ($d_{11}$, $d_{12}$) shown in FIG. 14 are obtained by analyzing the frequency components; the amplitude of the frequency analysis result ($d_{12}$) obtained when displaying the specific content that the user is interested in is much larger than the amplitude of the frequency analysis result ($d_{11}$) obtained when displaying the content that the user is not interested in.

In other words, the relationship [amplitude obtained when browsing a content that the user is interested in]>[amplitude obtained when browsing a content that the user is not interested in] is established. This indicates that a vibration, referred to as intention tremor, is generated when the user browses a content that he (or she) is interested in.

The effect of the intention tremor appears in the frequency band of about 3 Hz to 5 Hz when the terminal 100 is held by the user in the state shown in FIG. 15, and the frequency band in which the effect of the intention tremor appears varies depending on the posture of the user.

Figure 16:
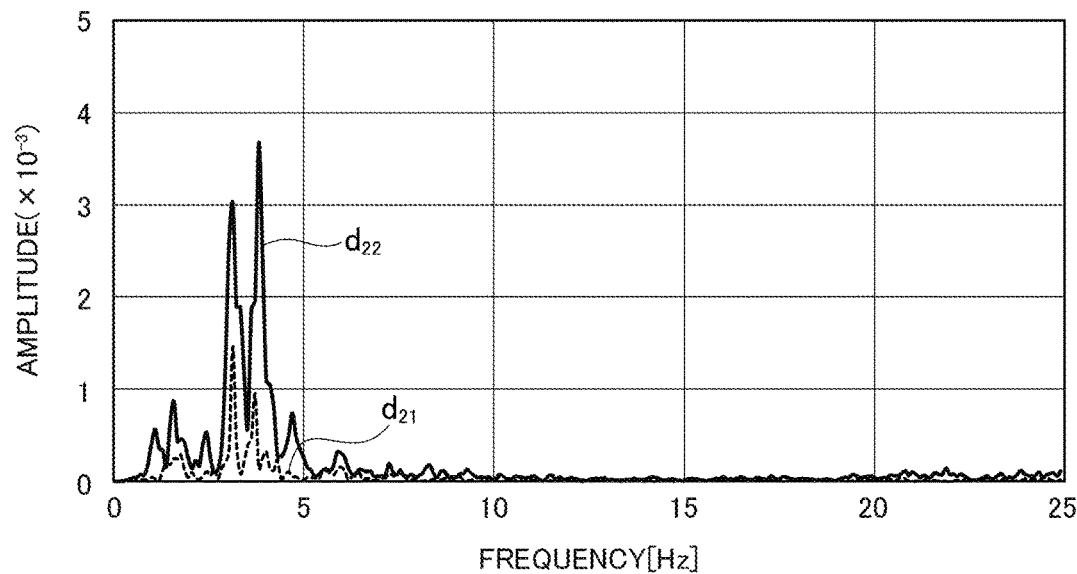
FIG. 16 is a graph showing a comparison between two frequency analysis results obtained when a specific subject (subject A) is interested and not interested, according to the third embodiment.
Figure 17:
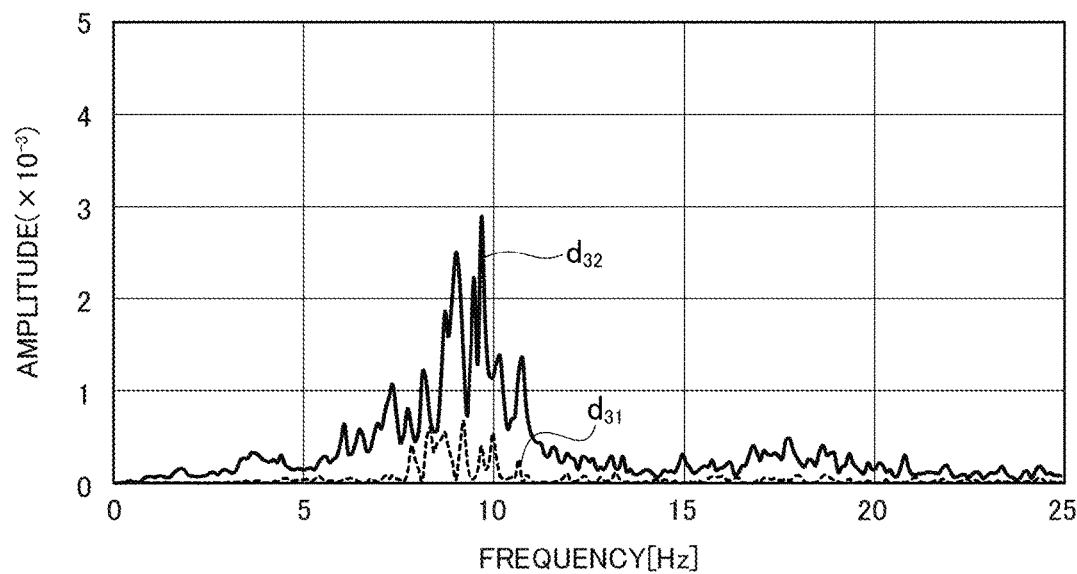
FIG. 17 is a graph showing a comparison between two frequency analysis results obtained when another specific subject (subject B) is interested and not interested, according to the third embodiment.

FIG. 16 and FIG. 17 show examples of frequency bands in which the effect of the intention tremor appears.

The analysis results ($d_{21}$, $d_{22}$) shown in FIG. 16 represent a frequency analysis result ($d_{22}$) obtained when a content that the user is interested in is displayed and a frequency analysis result ($d_{21}$) obtained when a content that the user is not interested in is displayed, in the case where the contents are displayed on the terminal 100 in a state in which the terminal 100 is held by the entire palm of the hand of the user with the elbow in contact with the desk 400, as shown in FIG. 15. Similar to the example of FIG. 14, in the example of FIG. 16, a large variation in amplitude value occurs in the frequency band of about 3 Hz to 5 Hz.

The analysis results ($d_{31}$, $d_{32}$) shown in FIG. 17 represent a frequency analysis result ($d_{32}$) obtained when a content that the user is interested in is displayed and a frequency analysis result ($d_{31}$) obtained when a content that the user is not interested in is displayed, in the case where the contents are displayed on the terminal 100 in a state in which the terminal 100 is supported and held by a seated user with only his (or her) fingers. In the example of FIG. 17, a large variation in amplitude value occurs in a frequency band of 3 Hz to 20 Hz. In particular, in a range 7 Hz to 11 Hz of the range of 3 Hz to 20 Hz, a large amplitude value is generated in the frequency analysis result ($d_{32}$) when the content that the user is interested in is displayed, which means that the intention tremor largely appears in the range of 7 Hz to 11 Hz.

Further, although not shown in the attached drawings, when the user holds the terminal 100 while he (or she) is standing, the intention tremor appears in a frequency band of about 1 Hz; so that, in the frequency band of about 1 Hz, a relatively large variation occurs between the frequency analysis result obtained when a content that the user is interested in is displayed and the frequency analysis result obtained when a content that the user is not interested in is displayed.

Considering the aforesaid various postures of the user, in the present embodiment, it is preferable to estimate whether or not the user has interest in a content by discriminating that there is a variation in amplitude in a frequency band from 1 Hz to 20 Hz.

As described above, according to the third embodiment of the present invention, estimation of the interest in a specific content displayed on the terminal 100 can be performed satisfactorily based on the difference of the intention tremor from a case where another content is displayed.

The frequency analysis examples shown in FIG. 14, FIG. 16, and FIG. 17 for estimating whether or not the user has interest are all examples in which whether or not the user has interest is estimated using both the terminal 100 and the auxiliary terminal 300, and the difference between the frequency detected by the terminal 100 and the frequency detected by the auxiliary terminal 300 is obtained. It is preferable to use both the terminal 100 and the auxiliary terminal 300 as described above; however, the same frequency analysis result can also be obtained in the case where only the terminal 100 described in the first embodiment is used.

5. Modifications

In the above embodiments, a smartphone is used as the terminal 100, and a smartwatch is used as the auxiliary terminal 300; however, other terminals having a three-axis acceleration sensor built therein, such as a tablet terminal, may be used.

Further, in the above embodiments, processes from the acceleration data acquisition process to the data processing process for evaluation are all performed in the terminal 100; however, some or all of the processes from the acceleration data acquisition process to the evaluation process may be performed externally by the server 200 or the like. For example, the terminal 100 performs frequency analysis of the acceleration data and calculates the average value, and transmits the integral value of the calculated average value to the server 20 where the server 20 performs the evaluation process.

Further, in each of the above embodiments, the results of the frequency analysis are ensemble averaged, and the obtained average value is integrated to obtain an amplitude integral value; however, other average values may be obtained instead. Further, in each of the above embodiments, when obtaining the amplitude integral value of the average for each frequency, the integral value is obtained for a period while the content is being browsed; however, the integral value may be obtained for a predetermined period (for example, a predetermined time such as one minute or three minutes) from the time browsing the content.

Further, the processes described in each of the above embodiments are executed by a program implemented in the terminal 100 or the like; however, the present invention also includes a configuration in which a program for executing the aforesaid processes is prepared, and the prepared program is implemented in an existing terminal such as a smartphone to thereby configure the psychological evaluation device described in each of the above embodiments. In such a case, the program to be implemented in the terminal can be transmitted to the terminal via various recording media or networks.

Further, in each of the embodiments described above, the evaluation process is performed for evaluating the interest of the user in an electronic content (electronic comics, electronic book or the like) displayed on the screen by the display 101 of the terminal 100. However, the evaluation process may be performed to evaluate the interest of the user, for example, when the user is viewing a content used integrally with with the terminal 100. For example, evaluation process for evaluating the interest of the user in a paper book (comic book, magazine, or other book) placed on the terminal 100 may be performed based on the output of the three-axis acceleration sensor 105 built in the terminal 100 (and the auxiliary terminal (smartwatch) 300).

When the terminal 100 is used for browsing the paper book, the terminal 100 may be made small enough to be inserted into the book, so that the paper book (the content) and the terminal 100 can be used integrally.

REFERENCE SIGNS LIST 100 terminal (smartphone)
101 display
101a screen
102 central processing unit (CPU)
103 ROM
104 RAM
105 three-axis acceleration sensor
106 wireless communication unit
107 short-distance wireless communication unit
111 acceleration data acquisition unit
112 low-frequency component acquisition unit
113 high-frequency component acquisition unit
114 gravity component acquisition unit
115 frequency analysis unit
116 average calculation unit
117 evaluation unit
200 server
201 network interface
202 user management unit
203 content storage
300 auxiliary terminal (smartwatch)
301 display
301a screen
302 central processing unit (CPU)
303 ROM
304 RAM
305 three-axis acceleration sensor
306 short-distance wireless communication unit

The invention claimed is:

1. A psychological evaluation device that estimates interest of a subject in a content used integrally with a terminal held by the subject, comprising:
an acceleration data acquisition unit that acquires first acceleration data obtained by a first acceleration sensor built in the terminal;
a frequency analysis unit that performs a frequency analysis on the first acceleration data in a gravity direction; and
an evaluation unit that estimates, when the terminal displays a specific content, the interest of the subject in the specific content based on a result of the frequency analysis obtained by the frequency analysis unit.

2. The psychological evaluation device according to claim 1, wherein
the acceleration data acquisition unit acquires second acceleration data obtained by a second acceleration sensor built in an auxiliary terminal worn on an arm of the subject, in addition to the first acceleration data obtained by the first acceleration sensor built in the terminal, and obtains difference data between a first piece of low-frequency data and a second piece of low-frequency data, the first piece of low-frequency data from the first acceleration data obtained by the first acceleration sensor built in the terminal, and the second piece of low-frequency data from the second acceleration data obtained by the second acceleration sensor built in the auxiliary terminal worn on the arm of the subject, and
the frequency analysis unit performs the frequency analysis on the difference data.

3. The psychological evaluation device according to claim 1, wherein the frequency analysis unit performs the frequency analysis on the first acceleration data of a dynamic acceleration component in the gravity direction at least in a band from 1 Hz to 20 Hz.

4. The psychological evaluation device according to claim 1, wherein the evaluation unit estimates that the subject is interested in the specific content when, among integral values of an average of each frequency component in the result of the frequency analysis, a peak integral value is a first value, and that the subject is not interested in the specific content when the peak integral value is a second value larger than the first value.

5. The psychological evaluation device according to claim 1, further comprising:
an average calculation unit that calculates an average of each frequency component obtained by performing the frequency analysis by the frequency analysis unit, for a predetermined time,
wherein the evaluation unit estimates that the subject is interested if an integral value of the average of each frequency component calculated by the average calculation unit is smaller than an integral value of the average obtained when the terminal displays a content other than the specific content.

6. A psychological evaluation method for estimating interest of a subject in a content used integrally with a terminal held by the subject, comprising:
an acceleration data acquisition process for acquiring first acceleration data obtained by a first acceleration sensor built in the terminal;
a frequency analysis process for performing a frequency analysis on the first acceleration data in a gravity direction; and
an evaluation process for estimating, when the terminal displays a specific content, the interest of the subject in the specific content based on a result of the frequency analysis obtained in the frequency analysis process.

7. The psychological evaluation method according to claim 6, wherein
the acceleration data acquisition process acquires second acceleration data obtained by a second acceleration sensor built in an auxiliary terminal worn on an arm of the subject, in addition to the first acceleration data obtained by the first acceleration sensor built in the terminal, and obtains difference data between a first piece of low-frequency data and a second piece of low-frequency data, the first piece of low-frequency data from the first acceleration data obtained by the first acceleration sensor built in the terminal, and the second piece of low-frequency data from the second acceleration data obtained by the second acceleration sensor built in the auxiliary terminal worn on the arm of the subject, and
the frequency analysis process performs the frequency analysis on the difference data.

8. The psychological evaluation method according to claim 6, further comprising:
an average calculation process for calculating an average of each frequency component obtained by performing the frequency analysis in the frequency analysis process, for a predetermined time,
wherein the evaluation process estimates that the subject is interested if an integral value of the average of each frequency component calculated in the average calculation process is smaller than an integral value of the average obtained when the terminal displays a content other than the specific content.

9. A non-transitory computer readable medium storing a program for causing a computer to execute a psychological evaluation or estimating interest of a subject in a content used integrally with a terminal held by the subject, the program causing the computer to execute:
- an acceleration data acquisition procedure for acquiring first acceleration data obtained by a first acceleration sensor built in the terminal;
- a frequency analysis procedure for performing a frequency analysis on the first acceleration data in a gravity direction; and
- an evaluation procedure for estimating, when the terminal displays a specific content, the interest of the subject in the specific content based on a result of the frequency analysis obtained in the frequency analysis procedure.

10. The non-transitory computer readable medium according to claim 9, wherein
- the acceleration data acquisition procedure acquires second acceleration data obtained by a second acceleration sensor built in an auxiliary terminal worn on an arm of the subject, in addition to the first acceleration data obtained by the first acceleration sensor built in the terminal, and obtains difference data between a first piece of low-frequency data and a second piece of low-frequency data, the first piece of low-frequency data from the first acceleration data obtained by the first acceleration sensor built in the terminal, and the second piece of low-frequency data from the second acceleration data obtained by the second acceleration sensor built in the auxiliary terminal worn on the arm of the subject, and
- the frequency analysis procedure performs the frequency analysis on the difference data.

11. The non-transitory computer readable medium according to claim 9, the program further causing the computer to execute:
- an average calculation procedure for calculating an average of each frequency component obtained by performing the frequency analysis in the frequency analysis procedure, for a predetermined time,
- wherein the evaluation procedure estimates that the subject is interested if an integral value of the average of each frequency component calculated in the average calculation procedure is smaller than an integral value of the average obtained when the terminal displays a content other than the specific content.

* * * * *